(12) United States Patent
Heimann et al.

(10) Patent No.: US 6,620,707 B1
(45) Date of Patent: Sep. 16, 2003

(54) HEAT CONDUCTOR, ESPECIALLY FOR A SENSOR, AND METHOD FOR PRODUCING SUCH A HEAT CONDUCTOR

(75) Inventors: Detlef Heimann, Gerlingen (DE); Bernd Reinsch, Ludwigsburg (DE); Alexander Bischoff, Eberdingen (DE); Juergen Werner, Leinfelden-Echterdingen (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/787,081

(22) PCT Filed: Jun. 15, 2000

(86) PCT No.: PCT/DE00/01990
§ 371 (c)(1),
(2), (4) Date: Sep. 5, 2001

(87) PCT Pub. No.: WO01/04915
PCT Pub. Date: Jan. 18, 2001

(30) Foreign Application Priority Data

Jul. 13, 1999 (DE) .......................... 199 32 545

(51) Int. Cl.$^7$ ................................ C22C 5/04
(52) U.S. Cl. ............... 438/469; 428/472.2; 420/466; 420/467; 148/430; 148/537; 204/228.6
(58) Field of Search .............. 428/469, 472.2; 148/430, 537; 420/466, 467; 204/424, 228.6

(56) References Cited

U.S. PATENT DOCUMENTS

| | | | | |
|---|---|---|---|---|
| 4,500,412 A | * | 2/1985 | Takahashi et al. | ........... 204/408 |
| 4,863,583 A | * | 9/1989 | Kurachi et al. | ............. 204/424 |
| 5,142,266 A | | 8/1992 | Friese et al. | |
| 5,787,866 A | | 8/1998 | Sano et al. | |
| 6,274,016 B1 | * | 8/2001 | Hasei et al. | ................. 204/291 |

FOREIGN PATENT DOCUMENTS

EP  0 859 233  8/1998

OTHER PUBLICATIONS

Patent Abstracts of Japan, vol. 012, No. 132 (C–490), Apr. 22, 1988 & JP 62 250151 A (Alps Electric Co. Ltd.), Oct. 31, 1987.
Patent Abstracts of Japan, vol. 1996, No. 03, Mar. 29, 1996 & JP 07 290198 A (Nittetsu Hard KK), Nov. 7, 1995.

* cited by examiner

Primary Examiner—John J. Zimmerman
Assistant Examiner—Jason Savage
(74) Attorney, Agent, or Firm—Kenyon & Kenyon

(57) ABSTRACT

A heating conductor, in particular for a sensor for determining at least one gas component in the exhaust gases of internal combustion engines. The heating conductor formed from a cermet which contains platinum, at least one metal oxide, and at least two further precious metals. A method for manufacturing the heating conductor by applying a paste containing a platinum powder, a metal oxide powder, and at least two further precious metals, to a ceramic foil and sintering the paste and ceramic foil combination.

19 Claims, 1 Drawing Sheet

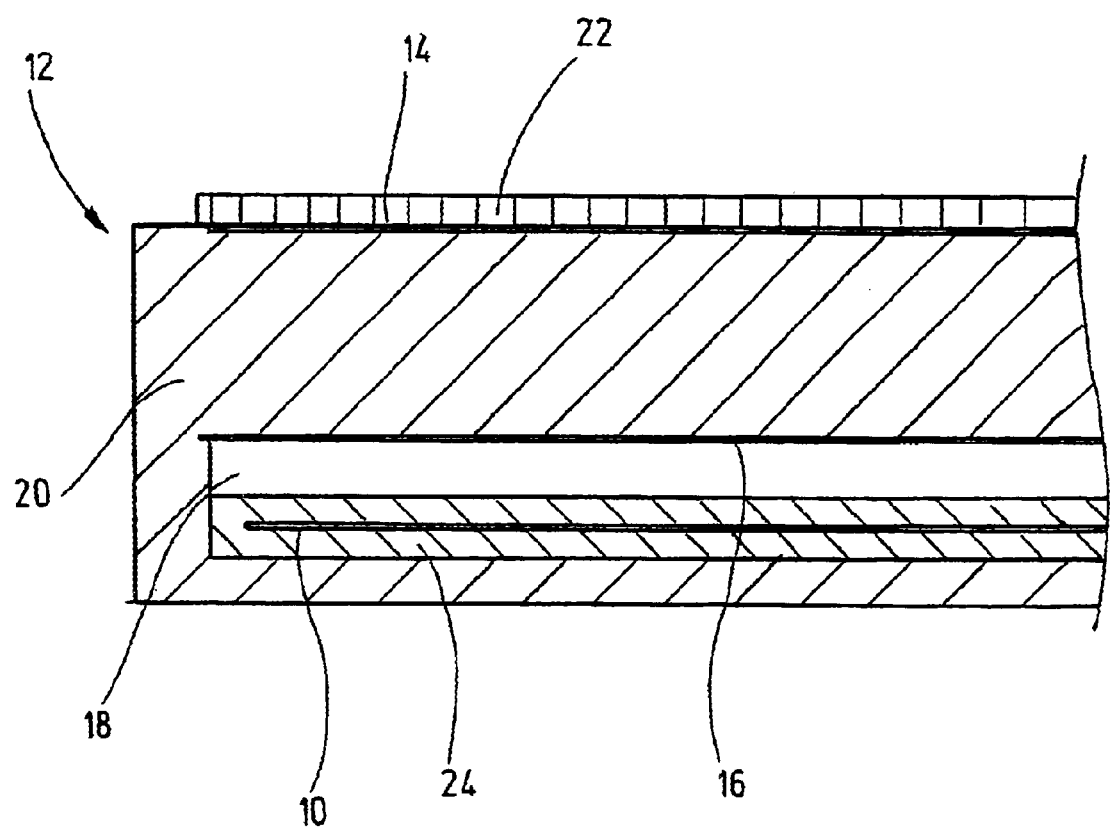

HEAT CONDUCTOR, ESPECIALLY FOR A SENSOR, AND METHOD FOR PRODUCING SUCH A HEAT CONDUCTOR

FIELD OF THE INVENTION

The present invention relates to a heating conductor, in particular for a sensor, and a method for manufacturing the heating conductor.

BACKGROUND INFORMATION

Heating conductors of the type mentioned are known and are used for setting an adjustable operating temperature of the sensor. Sensors of this type are marked by an advantageously layered design, individual layers being obtained using silk-screen printing, laminating, stamping, sintering, or the like. If the sensor acts to determine an oxygen concentration from the exhaust gases of an internal combustion engine, it contains essentially the following features:

A measuring electrode is arranged on a surface of the sensor and, if appropriate, is covered by a porous protective layer. Underneath the measuring electrode is located a layer composed of a solid electrolyte, that layer being followed by a reference electrode. The reference electrode in turn is situated on a reference gas channel, which is filled with a reference gas. To bring the sensor element to a specifiable temperature, there is arranged underneath the reference gas channel the heating conductor, which is optionally covered by an electrical insulator. The electrodes and the heating conductor are usually manufactured by sintering a mixture made of a metal oxide powder and a metal powder (cermet).

In manufacturing a sensor of this type, it is necessary, for one thing, to ensure that the measuring and reference electrodes have sufficient porosity, because—without going into greater detail here concerning a mode of functioning of a sensor of this type—a sufficiently large 3-phase boundary surface must be provided for assuring functionality. In order to prevent the measuring and reference electrodes from becoming densely sintered (no porosity), correspondingly low sintering temperatures must therefore be selected.

For another thing, the heating conductor must have a sufficient current carrying capacity, which is all the more beneficial, the lower the porosity of the heating conductor. Therefore, for manufacturing the heating conductor, the highest possible sintering temperature is preferred.

Known heating conductors are usually made of a cermet composed of platinum and a metallic oxide, such as aluminum oxide. From U.S. Pat. No. 5,787,866, it is known to manufacture the heating conductor out of platinum Pt and a further precious metal from the group Rh, Pd, Ir, Ru, and Os, in order to increase its resistance to corrosive processes. Since the measuring and reference electrodes preferably also contain platinum as a metallic component, the sintering temperature can only be selected as a compromise between the two objectives with respect to porosity.

Furthermore, it is disadvantageous that the known heating conductors have only insufficient operating stability on account of the oxidation of the platinum and the coagulation of the Pt. Because of aging processes of this type, the sensor can be subject to a total failure.

It is also disadvantageous that in manufacturing the known heating conductors using sintering, it is difficult to control the influence on the heating conductor resistance of unavoidable temperature differences in the sintering furnace as well as of the duration of a temperature treatment.

SUMMARY OF THE INVENTION

The aforementioned disadvantages are eliminated using a heating conductor manufactured with a cermet that has added to it at least two further precious metals, thereby allowing a lower sintering temperature. A lower sintering temperature creates a heating conductor with a low porosity, and, reduces the influence of temperature fluctuations in the sintering furnace. Furthermore, a heating conductor of this type demonstrates a significantly lower susceptibility to oxidation, so that the heating conductor has an increased service life.

It has proven to be particularly advantageous to select the further precious metals from the group Pd, Rh, Au, Ag, and Ir. In this context, the cermet should have the composition (a) 0.5 to 50% wt metal oxide, (b) 35 to 95% wt platinum, (c) 0.5 to 30% wt of the further precious metals, the cited quantities referring to the overall quantity of components (a), (b), and (c). In particular, a composition of the cermet of 6.6% wt Rh and 3.3% wt Au, as well as either 88.1 % wt Pt and 2% wt $Al_2O_3$ or 80.7% wt Pt and 9.4% wt $Al_2O_3$, have proven to be especially advantageous with respect to the resistance and the manufacture of the heating conductor.

As a function of the embodiment of the sintering method and/or of a property of the metals used for manufacturing the cermet, it is possible to influence the distribution of the metal components in the cermet. Thus it is conceivable that cermets in which heterogeneous alloys of platinum and the further precious metals are present are manufactured in a controlled manner. In this manner, the resistance of the heating conductor can additionally be influenced.

In addition, the method steps necessary in manufacturing the heating conductor with respect to the use of platinum-precious metal alloys can be developed in an advantageous manner. Thus, during the sintering, precious metals can precipitate out in the area of the measuring and reference electrodes due to their high vapor pressure. As a result of an often high CO affinity of the precious metals, this can lead to a falsification of the measuring value of the sensor. This can be prevented during the sintering in the sintering furnace if a sufficiently large air exchange is assured, for example using a blower. In this context, it is advantageous to introduce in the sintering furnace condensation areas for the precious metal.

Another method provides that the sintering furnace be designed such that a temperature gradient is present within the sensor element in the furnace. In this context, the sensor is arranged in the sintering furnace such that the heating conductor is located in an area having the lowest temperature, so that the precious metal only condenses in this area.

BRIEF DESCRIPTION OF THE DRAWINGS

The accompanying FIGURE shows a cross-sectional view of a sensor including a heating conductor.

DETAILED DESCRIPTION

Sensor 12 has a heating conductor 10, which is surrounded by an electrical insulator 24. In addition, sensor 12 has a measuring electrode 14, which is optionally covered by a porous protective layer 22. Beneath measuring electrode 14 is a layer 20 made of a solid electrolyte and then a reference electrode 16. Reference electrode 16 in turn is situated on a reference gas channel 18 which is filled by a reference gas.

A sensor 12 of this type is usually used for determining an oxygen concentration, in particular in exhaust gases of internal combustion engines. For this purpose, a potential, which fluctuates in accordance with the oxygen content in the exhaust gas at measuring electrode 14, is compared with a potential on reference electrode 16. The potential on reference electrode 16 is, inter alia, a function of the oxygen concentration in the reference gas and of the temperature. An adjustment of the temperature can be achieved using heating conductor 10.

The mode of functioning of a sensor 12 of this type is known, and in this connection it therefore only needs to be stated that measuring and reference electrodes 14, 16 must have sufficient porosity in order to have a sufficiently large 3-phase boundary surface. Stated in simplified form, the adjustment of the potential of measuring and reference electrodes 14, 16 takes place in the area of 3-phase boundary surface.

Furthermore, for assuring a sufficient current carrying capacity of heating conductor 10, it is necessary to keep its porosity as low as possible. The porosity can be substantially influenced by the level of the sintering temperature. High sintering temperatures, in this context, lead to a dense sintering of heating conductor 10, but also of electrodes 14, 16.

Sensor 12 is marked by its advantageously layered construction, the individual layers being obtained by silk-screen printing, laminating, stamping, sintering, or the like. In silk-screen printing, in this context, pastes are applied to a ceramic foil, which, after the sintering, form the individual layers. Electrodes 14, 16 and heating conductor 10, in this context, are formed from layers that are composed of a cermet, a metal oxide being used as the support structure and a metal being used as the conductor. For this purpose, a paste made of a metallic powder and a metallic oxide powder, producing the layer, is applied to a substrate and is then sintered.

In known sensors 12, platinum is used as a metal for heating conductor 10 and electrodes 14, 16, and aluminum oxide is preferred as a ceramic material in heating conductor 10. In electrodes 14, 16, $ZrO_2$ is used as the ceramic material.

By mixing at least two further precious metals in the paste that is to form heating conductor 10, the dense sintering of heating conductor 10 can be realized at a substantially lower sintering temperature than is the case when pure platinum is used. After the sintering, an at least ternary platinum-precious metal alloy exists.

The further precious metals are selected from the group Pd, Rh, Au, Ag and Ir. Overall, the cermet should have a composition of (a) 0.5 to 50% wt metal oxide, (b) 35 to 95% wt platinum, (c) 0.5 to 30% wt of the further precious metals, the aforementioned quantities referring to the overall quantity. In this context, a cermet having the composition Pt 88.1% wt, $Al_2O_3$ 2% wt, Rh 6.6% wt and Au 3.3% wt demonstrated a resistance of 3.6Ω. If the concentration of $Al_2O_3$ rose to 9.4 % wt and the concentration of Pt dropped to 80.7% wt, then the resistance rose to 9Ω.

The proportion of metal oxide, specifically aluminum oxide, in the cermet amounts to 0.5 to 50% wt. In this context, it was demonstrated that, independent of an increase of the resistance of heating conductor 10 as a result of an increased proportion of ceramic material, an additional increase in the resistance occurs as a result of the addition by alloying.

The precious metals can be introduced into the method in various ways. Thus, it is possible to add them to the paste directly as a powder. In addition, it is possible to use platinum powder to which precious metals have already been added or to apply the precious metals as a layer on the grains of the platinum powder, for example using chemical processes or pulverization. The latter method can result in the fact that the alloy, which preferably melts at a lower temperature, forms during the sintering process only in one contact area of the grains, so that after the sintering there exists overall a heterogeneous, at least ternary platinum-precious metal alloy. This can be especially advantageous if the precious metals used would lead to a lowering of a temperature coefficient and therefore, assuming a given heating voltage, only a lower heating output could be achieved in the sensor element tip. By using a heterogeneous platinum-precious metal alloy, an effect of this type can be avoided to the greatest extent possible.

During the manufacturing of heating conductor 10, in particular in a sintering furnace, the sintering temperature is selected as a function of at least one of the melting temperatures of the precious metals or of the platinum-precious metal alloy. Since these temperatures are lower than the melting temperature of platinum, a dense sintering of heating conductor 10 occurs at already essentially lower temperatures. Due to the lower temperatures, existing measuring and reference electrodes 14, 16 are also prevented from losing their porosity.

During the sintering process, some of the precious metals used can pass over into the gas phase due to their partially high vapor pressure. The resulting precious metal vapors can in turn condense in various areas of sensor 12. Inter alia, this can occur in the area of measuring and reference electrodes 14, 16. Since precious metals, for example gold, have a very high affinity for gases such as carbon monoxide, it can result in a covering of a surface of electrodes 14, 16, and this can lead to falsified measuring results of sensor 12.

A poisoning of the electrodes in this manner can be avoided in two ways. First, during the sintering process, a sufficiently large air exchange must take place in the area of the substrate. For example, this can be brought about by using a suitable blower in the sintering furnace. The sintering furnace in such a case is advantageously equipped with a condensation area, at which the gaseous precious metals can be precipitated out.

Second, the sintering furnace can be designed such that, during the sintering process, it has a temperature gradient in the area of the ceramic foil and the temperature in the area of the paste forming heating conductor 10 is the lowest possible. Overall, using the two methods, a condensation of gaseous precious metals can be avoided in the area of measuring and reference electrodes 14, 16.

What is claimed is:

1. A heating conductor, comprising:
   a cermet including platinum, at least one metal oxide and at least two further precious metals.

2. The heating conductor as recited in claim 1, wherein the heating conductor is part of an exhaust gas sensor for an internal combustion engine.

3. The heating conductor as recited in claim 1 wherein the at least two further precious metals are selected from the group consisting of Pd, Rh, Au, Ag, and Ir.

4. The heating conductor as recited in claim 1, wherein the cermet has a composition of:
   (a) 0.5 to 50% wt metal oxide,
   (b) 35 to 95% wt platinum, and
   (c) 0.5 to 30% wt of the at least two further precious metals, the cited quantities referring to the overall quantity of the components (a), (b), and (c).

5. The heating conductor as recited in claim 4, wherein the metal oxide is aluminum oxide.

6. The heating conductor as recited in claim 4, wherein the cermet has a composition of 6.6% wt Rh, 3.3% wt Au, 2% wt $Al_2O_3$, and 88.1% wt Pt.

7. The heating conductor as recited in claim 4, wherein the cermet has a composition of 6.6% wt Rh, 3.3% wt Au, 9.4% wt $Al_2O_3$, and 80.7% wt Pt.

8. The heating conductor as recited in claim 1 wherein the platinum and the at least two further precious metals exist as a homogeneous alloy.

9. The heating conductor as recited in claim 1, wherein the platinum and the at least two further precious metals exist as a heterogeneous alloy.

10. A method for manufacturing a heating conductor comprising the steps
    applying a paste to a ceramic foil, wherein the paste includes a metal oxide powder, a platinum powder and at least two further precious metals; and
    subsequently sintering the ceramic foil and the paste at a sintering temperature;
    wherein the sintering temperature is a function of at least one of the melting temperatures of platinum and the at least two further precious metals.

11. The method as recited in claim 10, wherein the heating conductor is part of a sensor for determining an oxygen concentration in exhaust gases of internal combustion engines.

12. The method as recited in claim 10, wherein the at least two further precious metals are added to the paste as a powder.

13. The method as recited in claim 10, wherein the metal oxide powder includes aluminum oxide.

14. A method for manufacturing a heating conductor comprising the steps of:
    applying a paste to a ceramic foil, wherein the paste includes a metal oxide powder, and at least one of:
        a platinum powder and at least two further precious metals, and
        an at least ternary platinum-precious metal alloy; and
    subsequently sintering the ceramic foil and the paste at a sintering temperature;
    wherein the sintering temperature is a function of at least one of the melting temperatures of platinum, of one of the at least two further precious metals, and of the ternary platinum-precious metal alloy; and
    wherein the sintering takes place in a sintering furnace and an air exchange occurs during the sintering in proximity to the ceramic foil.

15. The method as recited in claim 14, wherein the sintering furnace has a condensation area, at which gaseous precious metals can precipitate out.

16. The method as recited in claim 14, wherein during the step of sintering, the sintering furnace has a temperature gradient in the area of the ceramic foil and a lowest possible temperature in the area of pastes forming the heating conductor.

17. A method for manufacturing a heating conductor comprising the steps of:
    applying a paste to a ceramic foil, wherein the paste includes a metal oxide powder, and at least one of:
        a platinum powder and at least two further precious metals, and
        an at least ternary platinum-precious metal alloy; and
    subsequently sintering the ceramic foil and the paste at a sintering temperature;
    wherein the sintering temperature is a function of at least one of the melting temperatures of platinum, of one of the at least two further precious metals, and of the ternary platinum-precious metal alloy; and
    wherein the at least two further precious metals are applied on a surface of grains of the platinum powder, using one of chemical processes and pulverization.

18. A method for manufacturing a heating conductor comprising the steps of:
    applying a paste to a ceramic foil, wherein the paste includes a metal oxide powder, and at least one of:
        a platinum powder and at least two further precious metals, and
        an at least ternary platinum-precious metal alloy; and
    subsequently sintering the ceramic foil and the paste at a sintering temperature;
    wherein the sintering temperature is a function of at least one of the melting temperatures of platinum, of one of the at least two further precious metals, and of the ternary platinum-precious metal alloy; and
    wherein the platinum powder and the at least two further precious metals are added to the paste in the form of a pulverized, ternary platinum-precious metal alloy.

19. A device, comprising:
    a heating conductor including a cermet including platinum, at least one metal oxide and at least two further precious metals.

* * * * *